United States Patent [19]

Cline et al.

[11] 4,166,087

[45] Aug. 28, 1979

[54] AUTOMATIC INTERMITTENT VAPOR DISPENSER

[75] Inventors: Lee S. Cline, Downey; Philip J. John, Los Alamitos, both of Calif.

[73] Assignee: Cline-Buckner, Inc., Cerritos, Calif.

[21] Appl. No.: 547,015

[22] Filed: Feb. 4, 1975

Related U.S. Application Data

[63] Continuation of Ser. No. 446,915, Feb. 29, 1974, abandoned, which is a continuation of Ser. No. 200,968, Nov. 22, 1971, abandoned.

[51] Int. Cl.² .............................................. B01F 3/04
[52] U.S. Cl. ...................................... 261/96; 239/56; 239/60; 261/30; 261/DIG. 17; 422/305; 422/306
[58] Field of Search ............. 239/6, 54, 56, 60, 41–43; 261/24, 26, 49, 95, 102, 30, DIG. 17; 43/129; 128/186, 187; 21/108, 109, 117, 121, 124, 122; 307/293

[56] References Cited

U.S. PATENT DOCUMENTS

| | | | |
|---|---|---|---|
| 2,474,565 | 6/1949 | Abbott | 261/98 |
| 2,481,296 | 9/1949 | Dupuy | 239/42 X |
| 2,510,126 | 6/1950 | Melcher et al. | 21/126 |
| 2,614,820 | 10/1952 | Boydjieff | 261/26 |
| 2,629,149 | 2/1953 | Yaffe | 21/108 |
| 2,759,714 | 8/1956 | Ayup | 261/24 |
| 2,783,085 | 2/1957 | D'Angio | 239/60 X |
| 2,937,419 | 5/1960 | Vaughn | 21/126 |
| 3,298,674 | 1/1967 | Gilbertson | 261/102 X |
| 3,633,881 | 1/1972 | Yurdin | 261/24 |
| 3,652,873 | 3/1972 | Roberts | 307/293 X |

*Primary Examiner*—Richard L. Chiesa
*Attorney, Agent, or Firm*—Albert L. Gabriel

[57] ABSTRACT

The present invention relates to an improved vapor dispenser and method that may be used for vapor-treating the air of a given area; the air-treating vapors containing such diverse elements as medicants, decongestants, inhalants, repellants, insecticides, bactericides, deodorants, and the like. The disclosed vapor dispenser may be described as a "semistatic" type, since it uses a static vapor generator that does not require a propellant, and uses automatic intermittent air movement for dispensing the accumulated vapors into the area to be treated by the vapors. Thus, the disclosed semistatic vapor dispenser continually provides the desired vapor concentration.

An improved static vapor generator is also disclosed, the improvement permitting the static vapor generator to produce vapors at a more uniform rate during its entire lifetime.

4 Claims, 5 Drawing Figures

AUTOMATIC INTERMITTENT VAPOR DISPENSER

This is a continuation of application Ser. No. 446,915, filed Feb. 29, 1974, now abandoned, which application is in turn a continuation of Ser. No. 200,968, filed Nov. 22, 1971, now abandoned.

BACKGROUND OF THE INVENTION

There is an ever-increasing need for air sanitation, for air freshening, for air medication, for air deodorizing, and the like, and there is also an ever-increasing need for insect control, for bacterial control, and for similar services. At present, there is a trend for such services and controls by means of airborne vapors, and for convenience of discussion all such services will be grouped under the caption "air treatment" and "air sprays".

In such air treatment by air sprays, it is important that the vapors remain in the air in given effective concentrations. Moreover, the vapors should be non-toxic to humans and to warm-blooded animals.

In the early days of such air treatment, the best procedure that was then available was to use a "hand gun" that atomized a suitable liquid; but improved methods now utilize a pressurized container that uses a product such as "Freon" or the like to propel the liquid into the air in the form of an aerosol. This so-called "active" propellant technique is becoming less desirable for a number of reasons; one of the most important of which is the need for storing a large inventory of such pressurized containers, with the ever-present danger of explosion. Another, and more pressing reason for the discontinuance of this active technique, is the recognition that the propellants are less safe to human beings than had previously been believed. Therefore, the active technique is no longer completely sanctioned.

Another air treatment technique, known as a "static" or "still" technique, does not use a pressurized propellant. Rather, this static technique depends upon the characteristic that many materials—particularly liquid—tend to boil, or evaporate, at ambient conditions of temperature and air pressure, thus providing a localized air treatment.

In an attempt to improve the above static dissemination of the vapors, and to provide a controlled dosage of vapor, a motor-driven fan has been used to disperse the vapors, but the continuous use of such a fan has generally required a wire that is plugged into an electrical outlet, and this wire has become objectionable from an appearance point of view and from a dust-collecting point of view. it also limits the use of such a dispenser to areas that are proximate electrical outlets. In other cases, the motor is energized by a battery, but the battery has to be extremely large, or else it has to be replaced unreasonably often. Further, such continuous blowing of air on the static vapor source generally causes evaporation and usage of the vapor generating material much faster than desired, and at a generally uncontrollable rate, thereby tending to cause undesirable concentrations of the vapors when the vapor source is fresh, and resulting in an undesirably short operative life of the vapor source, requiring the frequent replacement thereof.

OBJECTS AND DRAWINGS

It is therefore a principal object of the present invention to provide an improved vapor generator.

It is another object of the present invention to provide an improved semistatic vapor dispenser.

It is still another object of the present invention to provide an improved vapor dispenser that uses a static vapor generator.

It is further object of the present invention to provide a semistatic vapor dispenser that automatically and intermittently disemminates vapor into a given area.

It is a still further object of the present invention to provide an improved vapor dispenser for intermittently and automatically dispensing vapors from a static vapor generator.

It is a still further object of the present invention to provide an improved vapor dispenser having an electronic circuit for automatically and intermittently disseminating vapors.

The attainment of these objects and others will be realized from a study of the following description taken in conjunction with the drawings of which:

SYNOPSIS

Figure 1:
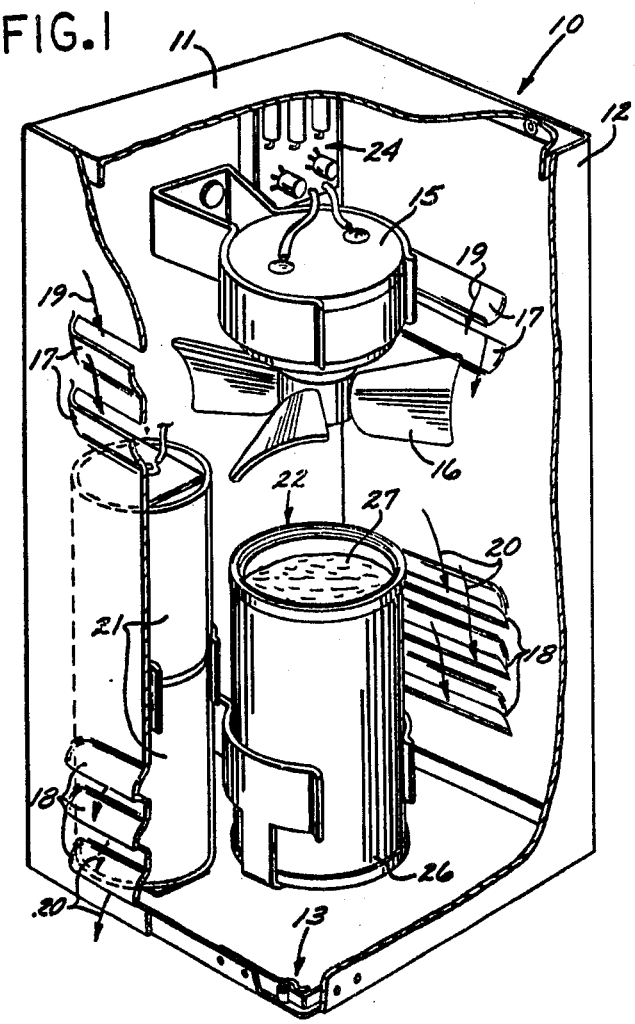
FIG. 1 shows a cutaway pictorial view of a vapor dispenser according to the present invention.

Broadly speaking, the present invention provides an improved semistatic vapor dispenser that uses a static vapor generator for providing an accumulation of vapors; and uses an electronic circuit for automatically turning on, and turning off, a motor/fan combination that disperses the accumulated vapors throughout the area to be vapor-treated.

An improved arrangement is disclosed for minimizing the recirculation of the vapor-laden air through the vapor dispenser, thus improving its effectiveness.

An improved static vapor generator is also disclosed, the improvement incorporating a "syneresis pad" that acts to provide more uniform vapor generation over the entire lifetime of the vapor generator.

INTRODUCTION

It will be advantageous, at this point, to discuss various types of static vapor generators that are in use. Of the many types that have been produced, one of the preferred forms uses a bottle that has been filled with the liquid to be vaporized, the bottle also containing a wick material whose capillary characteristic causes the liquid to rise up into the wick to a level at which the liquid may be evaporated into the air. In this way a suitable vapor is produced. The wick method has a number of disadvantages, among these being the fact that the evaporation is most rapid when the liquid level in the bottle is high, so that the effectiveness is reduced as the liquid level drops with use. Still another disadvantage of the wick method, and other conventional static techniques, is that they provide only localized dissemination of the vapor in the region immediately surrounding the vapor source.

It is apparent that frequently two or more of the above discussed air treatments are desired simultaneously, so it has become feasible to mix a plurality of liquids into a composite air treatment mixture, and to place this composite mixture in the air treatment bottle. Unfortunately, this mixture raises the problem that some of the liquids tend to clog up the wick so that the wick tends to lose its effectiveness after a period of use. Another disadvantage of such an air treatment mixture is that some of the air treatment liquids tend to evaporate, or vaporize, at different rates than others of the liquids. Therefore, at a given time, one of the liquids (e.g., one used for air sanitation) may be completely used up; whereas, another of the liquids (e.g., one used for perfuming the air) may still be available—thus causing the user to believe that the air treatment was still as efficacious, whereas it was not.

In an attempt to overcome the disadvantages of the wick/bottle arrangement, resort was made to a porous so-called "absorption block" that could be formed of wood, stone, ceramic, fiber, plastic, etc. By immersing such an absorption block into a suitable air treatment liquid or mixture, it would absorb a given volume thereof, and since the absorption block has a large "wicking area", the above discussed clogging up is minimized. However, the absorption block—and similar sachets—still has the inherent problem of different vaporizing rates, and, moreover, had its absorption volume limited by the size of the absorption block.

One approach to overcoming the problem of wicking and limited volume was to use the "drip" technique, wherein a bottle of liquid was inverted to permit the contained mixture of liquids to drip into a suitable recess for vaporization. This drip technique introduced the danger of leakage and spillage; and still had the problem of differential vaporization rates.

Still another approach was to form the air treatment materials into a solid compound whose exterior surface then vaporized to provide the desired vapor. This approach, while it solved some of the former problems, had its own difficulty in that the rate of vaporization decreased as the compound structure became physically smaller, so that reduced efficiency was inherent in the structure.

DESCRIPTION

As pointed out above, it is desirable to air-treat a given space by disseminating suitable vapors into such given space, the vapors preferably being produced by a static vapor generator. It has been found that such air treatments are required in many places, including for example, food markets, restaurants, kitchens, restrooms, dressing rooms, laboratories, retail stores, offices, waiting rooms, laundries, theaters, etc.

It has also been found that the requirements for these air treatments cover a wide range of situations, each being somewhat different from the others; typical requirements being, for example, materials such as insecticides, mild anesthesizing agents, decongestants, medicants, deodorants, and the like.

Therefore, it is desirable that the vapor dispenser disseminate any such material that may be desirable despite different vaporization rates, the length of usage of the vapor dispenser etc. Moreover, the vapor dispenser should operate effectively for an acceptable time period without requiring attention or maintenance.

The Vapor Dispenser

The above described desideratum may be achieved by the apparatus shown in the cutaway pictorial view of FIG. 1. This view shows a vapor dispenser 10 that is indicated to have a container body 11 that embodies suitable mounting holes, brackets, or other mounting means (not shown), permitting the dispenser 10 to be positioned at the desired location. A suitable container cover 12, which may be hingedly or otherwise attached to the container body 11, provides access to the inner portion of the dispenser, a suitable catch 13 being used to keep the container cover 12 closed during normal use.

Within the dispenser 10 is a small electric motor 15 and a motor-driven fan 16, which are preferably positioned in the upper portion of the container body 11. The dispenser 10 has a plurality of intake louvers 17 positioned at the upper portion of the container body 11, and has a plurality of exhaust louvers 18 positioned at the lower portion of the container body 11. Preferably, the top wall of the container body 11 is imperforate, so that it will serve as a dust shield for the motor and fan.

During the active portion of the vapor dispensing cycle, the motor 15 and fan 16 operate to draw air into the interior of the container as indicated by the intake arrows 19; and, since the motor and fan are at or above the level of the intake louvers 17, dust that may enter the dispenser 10 as indicated by intake arrows 19 will generally bypass the motor and fan, thereby protecting the motor and fan from dust that might otherwise limit their operation.

Disposition of the motor and fan in the upper portion of container body 11, in combination with placement of the static vapor generator in the lower portion of the container body, places the fan in a position wherein it will efficiently drive accumulated vapors from the inside of the container downwardly out through the louvers 18 during each cycle of motor operation, while at the same time blowing down on the static vapor source to accelerate vapor generation and to clear vapors from the immediate vicinity of the static vapor source during the relatively brief duration of a cycle of motor operation. The fan may be generally axially aligned with the static vapor source as illustrated in FIG. 1 so that it will blow directly down upon the static vapor source.

It will be noted that the intake louvers 17 have their open slots oriented upwardly, and that the exhaust louvers 18 have their open slots oriented downwardly. This differential louver orientation minimizes the probability of recirculating the airborne vapors through the container and encourages the dissemination of the vapors throughout the space to be treated, as indicated by exhaust arrows 20.

The dispenser, or dispensers 10, should be located so that the normal circulation of the air helps to disseminate the vapors throughout the space to be protected. As an illustration, the vapor dispenser should not be placed in such a location that an opened door causes air movement out of the room; rather, if located near a door, the dispenser should be located near one that causes air movement into the room. Similarly, dispenser placement near air conditioner outlets is preferable over locations near air conditioner intakes. These principles will provide improved air treatment and more efficient use of the vapors.

The interior of the dispenser 10 contains provision for replaceable batteries 21, as for example battery of the "D" size; and, in the lower portion thereof, also contains provision for holding or clamping a replaceable vapor generator 22 that will be more fully discussed later. An electronic circuit 24, that will also be discussed later in greater detail acts to automatically and intermittently turn on and turn off the fan/motor combination for predetermined time intervals.

The Vapor Generator

As indicated above, in the present invention the vapor generator 22 is preferably of the static type that does not require a pressurized propellant gas; and moreover, is preferably of a "gel" type.

Among the advantages of the gel type vapor generator are: they are convenient, they are non-spillable, they are easy to handle, they are readily stored, they are not dangerous, they may be used in any position, they may be formed into any desired shape, and their wide variety of formulations (to be discussed later) permits extreme flexibility of use.

As is known to those in the art, gels are made primarily of a "gelling" agents and liquid. Typically the gel will include, by weight, on the order of about 0.3% to 3.0% gelling about, 80% to 90% water, and various active liquid ingredients.

When such a gel is exposed to the air, the exposed exterior surface permits the liquids to vaporize; and in this way the desired vapors are generated, for dissemination throughout the space to be treated.

The Formulated Gel

As pointed out previously, various types of air treatment may be needed, either simultaneously or separately. For example, one location may require only air freshening; another location may require air medication; and still another location may need a deodorizing agent and a bactericide. Fortunately, there are presently available various volatile liquids suitable for these different purposes.

In the formulation of a gel, it therefore often becomes necessary to incorporate a number of the desired liquids into a liquid system; and to incorporate the liquid-system into the gel. Thus a gel may be formulated for any desired condition or combination of conditions. Since the gel comprises primarily liquid, the liquid system is quite adjustable; and may therefore contain medicants, decongestants, inhalants, repellants, insecticides, bactericides, aeromatics, perfumes, alcohol, eucalyptols, glycols, menthols, camphors, and/or the like. Moreover, due to the latitude permissible in formulating the gels, the various ingredients may be mixed in suitable proportions to achieve the desired lifetime in view of their vaporization rates, strengths, desired concentrations, and the like.

As the gel vaporizes, its resultant vapors tend to accummulate in the vicinity of the gel, but if air is blown across the gel, the vapors are removed—and the gel tends to vaporize at a faster rate. Therefore, in the formulation of the gel, it is desirable to take into account this overall vaporization rate and the vaporization conditions to be encountered.

Most gels, as mentioned above, are compounds of various liquids and a gelling agent such as CAB-O-SIL, Xantham, alginate, agar agar, gelatin, gum tragacanth, etc. Most of these gelling agents require heating in combination with the desired liquid ingredients to about 120° F., and then the heated material is poured into a container that provides the ultimate shape to the cooled congealed gel. This procedure is similar to the making of a gelatin dessert at home. Gels made with one of the newer gelling agents, KELZAN, are cold water formed.

Once the gel has its exterior surface exposed to the air, it begins to vaporize—and to contract—these contractions tending to squeeze liquid out of the gel. This effect is known as "syneresis", and will be discussed more fully later.

The Gel Body

The vapor generator 22 is preferably formed of a gel of the type discussed above, that has been poured into a receptacle 26 and permitted to harden to form a gel body 27. The presently preferred form of receptacle 26 for receiving the gel is a generally cylindrical can having a closed lid for preserving the gel, the lid being removable, as by means of a tear-off configuration, to activate the vapor generator. A "syneresis pad" 28, which will be described in detail hereinafter, is located in the bottom of the can in intimate contact with the gel body. The gel body 27 then begins to vaporize due to its exposure to the atmosphere. Since the vaporization takes place at the surface of the gel that is exposed to the air, after a short time the vapor generator 22 assumes the formation indicated in FIG. 2A, wherein the gel body 27 has begun to pull away inwardly from the sidewall of the can 26; and this has in turn enlarged the evaporative surface of the gel body 27 and also provided an annular air space into which the additional exterior surface of the gel body 27 may vaporize. As the vapors are formed, they flow out of the can and accumulate within the container 11. When the fan is turned on as indicated later, the vapors that have accumulated are dispensed; and the outflowing of vapor from the can is aided by the movement of the fan blown air; this having the effect of decreasing the concentration of the vapor proximate the can, and thus permitting further vaporization.

Figure 2A:
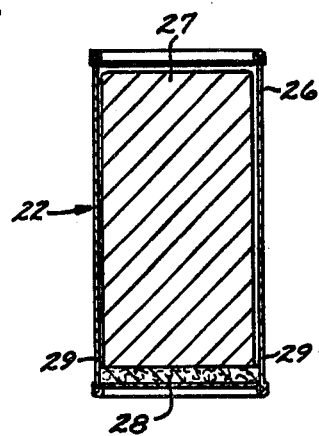
FIG. 2 shows various stages in the lifetime of a novel gel type vapor generator forming a part of the invention.
Figure 2B:
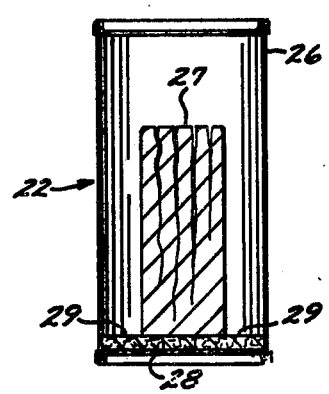

FIG. 2B indicates a later state in the life of the vapor generator 22; this figure indicating that an appreciable amount of the gel body 27 has vaporized, accumulated in the container body 11, and been blown into the space to be treated. The gel body 27 has assumed a generally cylindrical shape of substantially diminished diameter and height than before, but still having a large exterior surface that encourages vaporization of the liquids that formed the gel. Such exterior surface has been somewhat extended by cracks that have developed in the gel body.

The Syneresis Pad

At this point, the function of the syneresis pad 28 should be noted. As the gel body 27 reduces its diameter, the above mentioned syneresis action progressively squeezes the liquid ingredients out of the gel, and the synergized liquid ingredients tend to gravitate downwardly into the absorbent syneresis pad 28, regardless of their individual vaporization rates. The syneresis pad 28 is composed of a highly absorbent material, as for example a material having a blotter-like or felt-like consistency.

It will be realized that as the generally cylindrical gel body 27 reduces the diameter, its exterior surface area decreases, and this tends to decrease the rate of vapor generation. In the present invention, however, the syneresis pad 28 tends to compensate for this normally decreasing vapor generation rate; this being accomplished as follows.

Figure 2C:
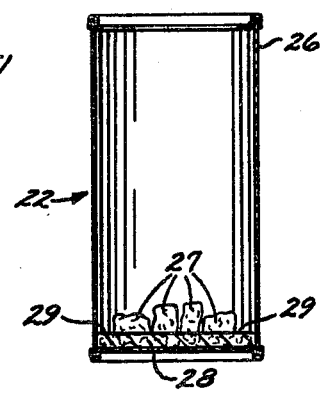

In FIG. 2A, practically none of the syneresis pad 28 is exposed. In FIG. 2B, however, an appreciable peripheral area 29 of the syneresis pad 28 is exposed. Thus, as the gel body 27 is used up, its reduced diameter exposes a progressively larger peripheral area 29 of the syneresis pad 28; and such exposed peripheral area of the syneresis pad 28 is now available for the vaporization of the liquids that have been absorbed by the syneresis pad 28. It will be noted that in FIG. 2C, which shows a still later state in the life of the gel body, almost the entire area of the syneresis pad 28 is available for vapor generation.

Thus, as the vaporization area of the gel body 27 decreases, the vaporization rate of the syneresis pad 28 increases; the increase generally compensating for the decrease. In this way, the vapor output concentration of the vapor generator 22 remains at a high level until most of the gel body has disappeared, with only small fragments remaining on the syneresis pad.

Electronic Circuitry

Figure 3:
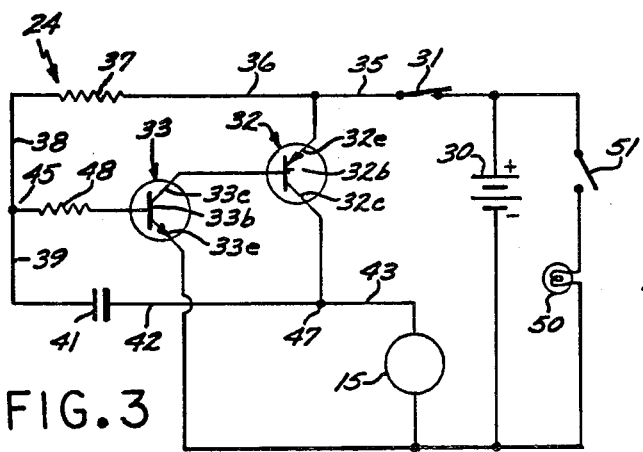
FIG. 3 shows a schematic drawing of an electronic circuit for automatically and intermittently energizing the fan motor illustrated in FIG. 1.

As pointed out above, the disclosed invention uses an electronic circuit 24 for intermittently and automatically turning the fan motor on and off; and the operation of the electronic circuit 24 will be understood from FIG. 3.

A power source 30, which may be two 1½ volt flashlight batteries arranged in series, is connected through a master switch 31 (if desired) to a circuit that has a first "switching" transistor 32, a second "timing" transistor 33, and a fan motor 15 as discussed above.

Each transistor has a combination of elements known as "emitters", "bases", and "collectors"—these being identified by suitable subscripts. For technical reasons, switching transistor 32 is of the type known as a PNP type, whereas the timing transistor 33 is of the type known as an NPN type. The one thing to be remembered about these two types of transistors is that a signal turns the transistor "on" when the signal has the same polarity as the center letter of the transistor type, and that a signal turns the transistor "off" when the signal has a polarity that is opposite to the center letter of the transistor type. Thus, a positive (P) signal turns on the NPN timing transistor 33 but turns off the PNP switching transistor 32. A negative signal (N) turns on the PNP switching transistor 32, but turns off the NPN timing transistor 33.

Circuit Operation

Assume that the master switch 31 has been closed to activate the circuit. For reasons that will become apparent from a later discussion, both transistors 32 and 33 are initially in their non-conductive states. Electricity flows from the plus terminal of the power source 30, through wires 35 and 36, through a "charging" resistor 37, through wires 38 and 39, through a "timing" capacitor 41, through wires 42 and 43, through the winding of the motor 15, and back to the negative terminal of the power source 30.

Due to the characteristics of the timing capacitor 41, it will not permit a continuous flow of DC current through the capacitor, but it will permit a charging current to flow through the above described loop. The amount of the charging current that flows through this loop is determined by a number of factors, the principal ones of which are the power source 30, the value of the charging resistor 37, and the size of the timing capacitor 41. For example, if the voltage of the power source is high, the charging current has a relatively large valve; if the valve of the charging resistor 37 is relatively large, the charging current is relatively small; and if the value of the timing capacitor 41 is relatively high, the charging current is also relatively high. Thus, by suitable design, the charging current of the capacitor 45 may be predetermined.

The OFF Time Interval

As the charging current flows, the voltage at takeoff point 45 changes; and, for the charging current discussed above, the voltage at takeoff point 45 rises. The above result may alternatively be described by saying that under the above discussed charging conditions, the takeoff point 45 develops a "positive-going" (P) electrical signal.

FIG. 3 shows that the takeoff signal produced at takeoff point 45 is applied to the base electrode 33b of the NPN timing transistor 33; and, since the applied signal is positive going (note that the positive-going P signal corresponds to the middle letter P of the "NPN" timing transistor 33), it eventually reaches a positive value that turns on the timing transistor 33.

Timing transistor 33, in turn, permits a negative-going N signal to appear at the base electrode 32b of the switching transistor 32. (Note that the negative-going N signal corresponds to the middle letter of the PNP switching transistor 32). Therefore, the negative-going N signal eventually reaches a value that causes the switching transistor 32 to become conductive.

As a result, after a given time interval after activating the circuit, electric current now flows directly from the power source 30, through the now conductive switching transistor 32, through the motor 15, and back to the power source. Thus, switching transistor 32 switches on the motor which is now completely energized, and rotates at its designed speed, causing its attached fan to draw air through the previously described vapor dispenser.

It is thus apparent that the above described charging circuit controls the OFF time interval, at the end of which the motor starts.

The ON Time Interval

The duration of the motor operation, i.e., the ON interval, is established as follows. It will be recalled that timing capacitor 41 has been charged up to a particular value at which the resultant takeoff signal at point 45 conductivated both of the transistors 32 and 33.

It will be noted from FIG. 3, that the now conductive switching transistor 32 is connected directly across the circuit formed by the charging resistor 37 and the timing capacitor 41; that is, the now conductive switching transistor 32 "shorts" this circuit. This shorting has two effects. The first such effect is that the timing capacitor 41 now tends to discharge itself by having its discharge current flow through the charging resistor 37 and the now conductive transistor 32 and to thus discharge the capacitor. However, since the charging resistor 37 is ordinarily of very high value (typically 15 megohms in order to provide the desired charging time), the discharging current flow through the resistor 37 is quite small.

The second effect of the shorting action of the now conductive switching transistor 32 is as follows. Its low resistance conductive state applies the positive voltage of power source 30 directly to point 47, which tends to cause the capacitor 41 to discharge more rapidly than indicated above.

It will be recalled that the timing transistor 33 is also conductive at this time and this has the following result.

The capacitor 41 thus tends to discharge through the discharge resistor 48, and through the now conductive timing transistor 33 to the negative terminal of the power source 30—this capacitor discharging action being aided by the high voltage at point 47. It should be noted that the discharging action is dependent, to a great extent, on the value of the discharging resistor 48, and since this resistor is not involved in the charging circuit, it may be selected to produce the desired discharge time.

Thus, the above described discharging action discharges capacitor 41, and as the discharging action takes place, the voltage at the takeoff point 45 decreases to produce a negative-going N signal. Eventually, the N signal at point 45 decreases to a value at which it turns off the NPW timing transistor 33. As the timing transistor 33 is turned off, it also turns off the switching transistor 32, and this in turn switches off the motor.

Thus, the above described discharging circuit controls the ON time interval, at the end of which the motor stops. The circuit 24 is now ready to initiate another charging action, at the end of which the motor is again switched on.

It may thus be realized that the above described charge-discharge circuits control the timing of the ON and the OFF intervals of the switching and timing transistors 32 and 33.

If desired, the circuit 24 of FIG. 3 may contain a battery tester that includes a test lamp 50 and a test switch 51 that selectively connects lamp 50 across the batteries, causing the test lamp to light up to a degree that is indicative of the state of charge of the battery.

It will thus be understood that the timing transistor 33 turns on and off in response to the charging and discharging action of the timing capacitor 41, and that within given limits, the ON and OFF time intervals are generally independent. The switching transistor 32 reacts to the state of the timing transistor 33, and switches the fan motor either on or off in accordance with the timing cycle.

In this way, the disclosed circuit automatically and intermittently activates the air-moving fan for predetermined ON and OFF time intervals. During the OFF time interval, the static vapor generator produces an accummulation of vapors in the container body 11; and during the ON time interval, the moving air expels the vapor-laden air to thus disseminate the vapors into the space to be treated. Due to the use of the intermittent air movement, and to the use of a static vapor generator, the disclosed vapor generator periodically disseminates the vapor-laden air, and may thus be designated as a "semistatic" unit.

Typical values for the above described circuit are as follows:

| | |
|---|---|
| charging resistor 37 | 15 megohms |
| timing capacitor 41 | 22 microfarads |
| discharging resistor 48 | 390 kilohms |
| switching transistor 32 | 2N5355 |
| timing transistor 33 | 2N3415 |
| ON time interval | 30 seconds |
| OFF time interval | 4 minutes |
| ON current | 20 milliamperes |
| OFF current | 2 microamperes |

These circuit values are given by way of illustration, and not of limitation. Such circuit values will produce ON and OFF times of about 30 seconds and 4 minutes, respectively, making a duty cycle less than about 13%.

Even with such a light duty cycle, the vapor accummulation mode of operation of the invention provides excellent vapor distribution. Additionally, such a light duty cycle allows both the vapor generator and the batteries to regenerate themselves during the OFF time interval.

SUMMARY

The disclosed vapor dispenser has many advantages over prior devices of this type. First of all, it uses a static vapor generator that does not require a pressurized propellant, and is thus safer to store and use. Second, the disclosed vapor generator has a novel feature that provides improved consistency of its vapor generation rate over the lifetime of the vapor generator. Third, an electronic circuit automatically and intermittently produces air movement for dissemination of the accummulated vapors. Fourth, the vapors may be formulated for the desired air treatment. Fifth, the intermittent operation of the air-moving motor/fan combination provides extended vapor generator life while maintaining efficient vapor dispensing. Sixth, the intermittent operation of the air-moving motor/fan combination permits the battery to regenerate itself during its OFF periods, and thus provides extremely long battery life. Seventh, the air movement through the vapor dispenser minimizes recirculation of the vapor-laden air in the vapor dispenser, thus improving its efficiency. Eighth, the movement of the air through the vapor dispenser minimizes the deposition of dirt on the motor, thus providing an improved motor operation. And finally, the disclosed vapor dispenser is practically maintenance-free, except for replacement of the exhausted vapor generator and batteries.

While the instant invention has been shown and described herein in what are conceived to be the most practical and preferred embodiments, it is recognized that departures may be made therefrom within the scope of the invention.

We claim:
1. A static vapor generator comprising;
    (A) a vapor producing gel body comprising
        a gelling agent;
        a coacting liquid system;
        a material portion of the liquids forming said liquid system being adapted for air treatment;
    (B) means for improving the uniformity of the vaporization rate of said vapor generator;
        said vaporization rate improving means comprising a syneresis pad whose exposed area increases as the exposed area of said gel body decreases;
        whereby the overall exposed area of said gel body and said syneresis pad tends to remain constant;
    (C) said gel body being positioned in contact with said syneresis pad;
        whereby liquid squeezed out of said gel body is absorbed by said syneresis pad.
2. The combination of claim 1 wherein said liquid system comprises at least one element selected from the class consisting of deodorants, bactericides, decongestants, inhalants, aromatics, insecticides, repellants, medicants, and pharmaceuticals.
3. A semistatic vapor dispenser comprising:
    static vapor generator means, adapted to generate vapors in a continuous manner, for providing an accumulation of vapors during a first given time interval;

air circulating means, comprising a motor and fan, for dispensing said accumulated vapors in the form of vapor-laden air into a given space during a second given time interval;

means for minimizing recirculation of said vapor-laden air through said vapor dispenser;

said recirculation minimizing means comprising a set of intake louvers having their open slots directed upwardly, and a set of exhaust louvers having their open slots directed downwardly; and means, comprising electronic circuitry for deactivating said air-moving means during said first given time interval, and for activating said air-moving means during said second given time interval;

said static vapor generator means comprising a gel body positioned in a receptacle that substantially confines the bottom and sides of the body;

said gel body being positioned in contact with a syneresis pad;

whereby liquid squeezed out of said gel body by syneresis is absorbed by said syneresis pad.

4. A vapor dispenser comprising:

static vapor generator means for providing an accumulation of vapors during a first given time interval;

air-moving means for dispensing said accumulated vapors into a given space during a second given time interval; and automatic means for intermittently deactivating and activating said air-moving means for said first and second time intervals to provide a plurality of dispensing cycles per hour of operation;

said static vapor generator means comprising a gel body in a receptacle that substantially confines the bottom and sides of the body;

said gel body comprising:
a gelling agent;
a coacting liquid system;
a material portion of the liquids forming said liquid system being adapted for air treatment;
means for improving the uniformity of the vaporization rate of said static vapor generator;
said vaporization rate improving means comprising a syneresis pad whose exposed area increases as the exposed area of said gel body decreases;
whereby the overall exposed area of said gel body and said syneresis pad tends to remain constant.

* * * * *